US008367718B2

(12) United States Patent
Fukui et al.

(10) Patent No.: US 8,367,718 B2
(45) Date of Patent: Feb. 5, 2013

(54) EPIGALLOCATECHIN GALLATE TRIMER AND α-GLUCOSIDASE INHIBITOR CONTAINING EPIGALLOCATECHIN GALLATE POLYMER

(75) Inventors: Yuko Fukui, Mishima-gun (JP); Takashi Iwashita, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 13/061,038

(22) PCT Filed: Aug. 28, 2009

(86) PCT No.: PCT/JP2009/065089
§ 371 (c)(1),
(2), (4) Date: Feb. 25, 2011

(87) PCT Pub. No.: WO2010/024396
PCT Pub. Date: Mar. 4, 2010

(65) Prior Publication Data
US 2011/0172300 A1 Jul. 14, 2011

(30) Foreign Application Priority Data
Aug. 29, 2008 (JP) ................................ 2008-222922

(51) Int. Cl.
*A61K 31/35* (2006.01)
(52) U.S. Cl. ...................................................... 514/456
(58) Field of Classification Search .................. 514/456
See application file for complete search history.

(56) References Cited

U.S. PATENT DOCUMENTS

| 5,629,338 | A | 5/1997 | Okuda et al. | |
|---|---|---|---|---|
| 6,294,190 | B1 | 9/2001 | Nakahara et al. | |
| 7,851,501 | B2 * | 12/2010 | Aydt et al. | 514/438 |
| 7,989,492 | B2 * | 8/2011 | Nakai et al. | 514/456 |
| 2008/0275258 | A1 * | 11/2008 | Nakai et al. | 549/399 |
| 2009/0186936 | A1 | 7/2009 | Moriguchi et al. | |

FOREIGN PATENT DOCUMENTS

| JP | 58032875 | A | 2/1983 |
|---|---|---|---|
| JP | 01102022 | A | 4/1989 |
| JP | 03219872 | A | 9/1991 |
| JP | 3228664 | A | 10/1991 |
| JP | 07061927 | A | 3/1995 |
| JP | 09040689 | A | 2/1997 |
| JP | 2000226329 | A | 8/2000 |
| JP | 2007060908 | A | 3/2007 |
| JP | 2007-176845 | | 7/2007 |
| JP | 2007231009 | A | 9/2007 |
| JP | 2008137925 | A | 6/2008 |
| JP | 2009-001531 | | 1/2009 |
| WO | WO-2004030440 | A2 | 4/2004 |
| WO | 2005/116005 | | 12/2005 |
| WO | WO2005116005 | * | 12/2005 |
| WO | WO-2007136015 | A1 | 11/2007 |

OTHER PUBLICATIONS

Nakai et al. CAS:144:22760, 2005.*
International Preliminary Report on Patentability issued Apr. 12, 2011, in PCT/JP2009-065089.
T. Masui et al., "'α-Glucosidase Inhibitory Action of Natural Acylated Anthocyanins. 2. α-Glucosidase Inhibition by Isolated Acylated Anthocyanins," *J. Agric. Food Chem.*, 49, pp. 1952-1956, 2001.
Extended European Search Report dated Apr. 3, 2012 in European Patent Application No. EP09810041.5.
M. Lorenz et al., "A Constituent of Green Tea, Epigallocatechin-3-gallate, Activates Endothelial Nitric Oxide Synthase by a Phosphatidylinositol-3-OH-kinase-, cAMP-dependent Protein Kinase-, and Akt-dependent Pathway and Leads to Endothelial-dependent Vasorelaxation", *Journal of Biological Chemistry*, vol. 279, No. 7, pp. 6190-6195, Nov. 2004.
S. Duffy et al., "Short- and Long-Term Black Tea Consumption Reverses Endothelial Dysfunction in Patients With Coronary Artery Disease", Circulation, *Journal of the American Heart Association*, vol. 104, pp. 151-156, Feb. 2001.
E. Anter et al., "Activation of Endothelial Nitric-oxide Synthase by the p38 MAPK in Response to Black Tea Polyphenols," *Journal of Biological Chemistry*, vol. 279, No. 45, pp. 46637-46643, Aug. 2004.
M. Nakai et al., "Inhibitory Effects of Oolong Tea Polyphenols on Pancreatic lipase in Vitro", *J. Agric. Food Chem.* 53, 4593-4598, Apr. 2005.
Hatano et al., "Flavan Dimers with Lipase Inhibitory Activiy from *Cassia Nomame*,"Phytochemistry, vol. 46, No. 5, 1997, pp. 893-900.
Korean Office Action dated Jul. 27, 2010, issued in Korean Application No. 10-2006-7026819 [in Korean].
Hashimoto et al., "Anti-AIDS agents. 24. Evaluation of Tea Polyphenols as Anti-HIV Agents," Bioorganic & Medicinal Chemistry Letters (1996), vol. 6, No. 6, pp. 695-700.
Hashimoto et al., "Evaluation of the Anti-oxidative Effect (in vitro) of Tea Polyphenols," Biosci. Biotechnol. Biochem., 67 (2), pp. 396-401, (2003).
Moreno et al., "Inhibitory Effects of Grape Seed Extract on Lipases," Nutrition 19, pp. 876-879, 2003.
Yoshikawa et al., "*Salacia reticulata* and its Polyphenolic Consitituents with Lipase Inhibitory and Lipolytic Activities Have Mild Antiobesity Effects in Rats," J. Nutri 132:1819-1824 (2002).
Han et al., "Anti-obesity action of oolong tea," International Journal of Obesity (1999) 23, pp. 98-105.
Iwata et al., "Effects of Oolong tea on Plasma Lipids and Lipoprotein Lipase Activity in Young Women," J. Jpn. Soc. Nutr. Food Sci. 44, (1991), pp. 251-259 (English Translation).

(Continued)

*Primary Examiner* — Rei-tsang Shiao
(74) *Attorney, Agent, or Firm* — Drinker Biddle & Reath LLP

(57) ABSTRACT

The present invention provides an α-glucosidase inhibitor containing a novel epigallocatechin gallate trimer and an epigallocatechin gallate polymer. Decomposition of starch derived from a meal and sugar derived from a polysaccharide can be suppressed by α-glucosidase inhibitory action, thus suppressing absorption. A food and drink excellent in α-glucosidase inhibitory action for suppressing sugar absorption and further for preventing diabetes for a long time can be provided by adding the α-glucosidase inhibitor to a food and drink.

11 Claims, 6 Drawing Sheets

OTHER PUBLICATIONS

Chin et al., "Clinical Efficacy of Oolong Tea on Anti-Simple Obesity" J. Japanese Soc. Clin. Nutri. (20(1):89-90 (1998) (English Translation).

Nakai et al., "Inhinitory Effects of Oolong tea Polyphenols on Pancreatic Lipase in Vitro," Agricultural and Food Chemistry, 2005, vol. 53, pp. 4593-4598.

International Search Report mailed Aug. 16, 2005 in PCT/JP2005/009666 filed May 26, 2005.

European Search Report issued Dec. 4, 2008, in EP Appln. No. 05743859.0.

F. Hashimoto et al., "Tannins and Related Compounds. XC.[1)] 8-C-Ascorbyl (−)-Epigallocatechin 3-O-Gallate and Novel Dimeric Flavan-3-ols, Oolonghomobisflavans A and B, from Oolong Tea. (3)", Chem. Pharm. Bull. vol. 37, No. 12, pp. 3255-3263, Dec. 1989.

T. Masui et al., "'α-Glucosidase Inhibitory Profile of Catechins and Theaflavins", J. Agric. Food Chem. vol. 55, pp. 99-105, 2007.

T. Masui et al., "α-Glucosidase Inhibitory Action of Natural Acylated Anthocyanins. 2. α-Glucosidase Inhibition by Isolated Acylated Anthocyanins," J. Agric. Food Chem., 49, pp. 1952-1956, 2001.

R. Kusano et al., "Polymer-Like Polyphenols of Black Tea and Their Lipase and Amylase Inhibitory Activities", Chem. Pharm. Bull. vol. 56, No. 3, pp. 266-272, 2008.

International Search Report mailed Oct. 13, 2009 in PCT/JP2009/065089 filed Aug. 28, 2009.

* cited by examiner

OHBF-Tri2

OHBF-Tri4

OHBF-tetramer1

EPIGALLOCATECHIN GALLATE TRIMER AND α-GLUCOSIDASE INHIBITOR CONTAINING EPIGALLOCATECHIN GALLATE POLYMER

CROSS REFERENCE TO RELATED APPLICATIONS:

This application is the National Stage of International Application No. PCT/JP2009/065089, filed Aug. 28, 2009, and claims benefit of Japanese Application No. 2008-222922, filed Aug. 29, 2008, which are herein incorporated by reference in their entirety.

TECHNICAL FIELD

The present invention relates to a novel epigallocatechin gallate trimer and an α-glucosidase inhibitor containing an epigallocatechin gallate polymer.

BACKGROUND ART

The α-glucosidase inhibitory substance inhibits α-glucosidase localized on the intestinal epithelium to suppress and delay decomposition/absorption of a saccharide. Thus, it has a suppressive action on elevation of blood sugar level. Therefore, the α-glucosidase inhibitory substance is useful for various diseases derived from chronic hyperglycemia, such as diabetes and adiposity. Since α-glucosidase inhibitory activity was found in a malt component in 1933, many α-glucosidase inhibitory substances derived from plants such as wheat and beans have been found.

In 1966, nojirimycin having α-glucosidase inhibitory activity was isolated from a microorganism metabolite and its structure was determined. An analogous compound thereof, 1-deoxynojirimycin, which was obtained from a mulberry-leaf extract, is known to have α-glucosidase inhibitory activity. A method for extracting it without reducing its activity is disclosed (Patent Literature 1).

Furthermore, it has been reported that a substance isolated from an extract of Kothalahimbutu's (Salacia reticulate) root and having a cyclitol structure of a 13-membered ring having a sulfoxide has high maltase inhibitory activity of 0.093 µM in terms of $IC_{50}$ (Patent Literature 2).

Furthermore, as the anthocyanin compounds isolated from the roots of morning glory and violet sweet potato, namely, diacylated pelargonidin ($IC_{50}$: 60-107 µM), cyanidin ($IC_{50}$: 193 µM) and 3-sophoroside-5-glucoside ($IC_{50}$: 200 µM) of peonidin, are reported to have maltase inhibitory activity (Non Patent Literature 1). Furthermore, substances such as theasinensin A (maltase inhibitory activity: 142 µM in terms of $IC_{50}$) contained in tea leaves, a theaflavin derivative having a galloyl group and proanthocyanidin having an epiafzelechin gallate as a structural unit are confirmed to have maltase inhibitory activity(Patent Literature 3). However, a theaflavin derivative having a galloyl group has a maltase inhibitory activity of 10 to 136 µM in terms of $IC_{50}$ but the content thereof in tea leaves is as extremely low as 0.1 to 0.2% (Non Patent Literature 2).

It has been reported that theaflavin of black tea and catechins of green tea have α-glucosidase inhibitory activity (Non Patent Literature 2). It is confirmed that (−)-epigallocatechin-3-O-gallate (hereinafter, also referred to as "EGCG") and (−)-epicatechin-3-O-gallate having a galloyl group at position 3 among the catechins, and theaflavin-3-O-gallate and theaflavin-3,3'-di-O-gallate among the theaflavins have the activity. With respect to the α-glucosidase inhibitory activity of black tea, the activities of its fractionated products and the like have been investigated. A fraction of a polymer whose polymerization degree is advanced by fermentation is also known to have the activity (Non Patent Literature 3).

Citation List
Patent Literature
  PTL 1: Japanese Patent Laid-Open No. 2007-60908
  PTL 2: Japanese Patent Laid-Open No. 2008-137925
  PTL 3: Japanese Patent Laid-Open No. 2007-231009
Non Patent Literature
  NPL 1: J. Agric. Food Chem. 2001, 49, 1952-1956
  NPL 2: J. Agric. Food. Chem., 55, 99-105, 2007
  NPL 3: Chem. Pharm. Bull. 56(3), 266-272, 2008

SUMMARY OF INVENTION

Technical Problem

Plant extracts and the like having α-glucosidase inhibitory activity have been reported as described above. However, for example, if an extract from a certain plant has a desired effect, as long as an active ingredient contained in the extract is not identified, it is difficult to stably provide an α-glucosidase inhibitor because it is derived from a naturally occurring product. Furthermore, in the case where an inhibitor derived from a low palatable plant is used as a food and drink, flavor and safety are presumably affected.

Solution to Problem

The present inventors focused on a component contained in tea daily taken in consideration of use as a food and drink and intensively conducted studies. As a result, they elucidated that an EGCG polymer suppresses the action of α-glucosidase. Of them, novel compounds, i.e., (2R,3R)-8-(((2R,3R)-8-(((2R,3R)-5,7-dihydroxy-3-(3,4,5-trihydroxybenzoyloxy)-2-(3,4,5-trihydroxyphenyl)chroman-6-yl)methyl)-5,7-dihydroxy-3-(3,4,5-trihydroxybenzoyloxy)-2-(3,4,5-trihydroxyphenyl)chroman-6-yl)methyl)-5,7-dihydroxy-2-(3,4,5-trihydroxyphenyl)chroman-3-yl 3,4,5-trihydroxybenzoate (hereinafter, referred to as "oolong homobisflavan-trimer-2"), (2R,3R)-8-(((2R,3R)-6-(((2R,3R)-5,7-dihydroxy-3-(3,4,5-trihydroxybenzoyloxy)-2-(3,4,5-trihydroxyphenyl)chroman-6-yl)methyl)-5,7-dihydroxy-3-(3,4,5-trihydroxybenzoyloxy)-2-(3,4,5-trihydroxyphenyl)chroman-8-yl)methyl)-5,7-dihydroxy-2-(3,4,5-trihydroxyphenyl)chroman-3-yl 3,4,5-trihydroxybenzoate (hereinafter, referred to as "oolong homobisflavan-trimer-4"), (2R,3R)-8-(H2R,3R)-8-(((2R,3R)-8-(((2R,3R)-5,7-dihydroxy-3-(3,4,5-trihydroxybenzoyloxy)-2-(3,4,5-trihydroxyphenyl)chroman-8-yl)methyl)-5,7-dihydroxy-3-(3,4,5-trihydroxybenzoyloxy)-2-(3,4,5-trihydroxyphenyl)chroman-6-yl)methyl)-5,7-dihydroxy-3-(3,4,5-trihydroxybenzoyloxy)-2-(3,4,5-trihydroxyphenyl)chroman-6-yl)methyl)-5,7-dihydroxy-2-(3,4,5-trihydroxyphenyl)chroman-3-yl 3,4,5-trihydroxybenzoate (hereinafter, referred to as "oolong homobisflavan-tetramer-1"), and (2R,2'R,3R,3'R)-8,8'-(2R,2'R,3R,3'R)-8,8'-methylenebis(5,7-dihydroxy-3-(3,4,5-trihydroxybenzoyloxy)-2-(3,4,5-trihydroxyphenyl)chroman-8,6-diyl)bis(methylene)bis(5,7-dihydroxy-2-(3,4,5-trihydroxyphenyl)chroman-8,3-diyl) bis(3,4,5-trihydroxybenzoate) (hereinafter, referred to as "oolong homobisflavan-tetramer-2") have significant inhibitory activity, which was stronger than those of an EGCG monomer, an EGCG dimer such as a theaflavin, and TSN-A. In particular, oolong homobisflavan-trimer-4 and oolong homobisflavan-tetramer-1 were confirmed to have inhibitory activity 10 times as large as the EGCG monomer. Furthermore, among the dimers, TSN-D and oolong homobisflavan-B were found to have strong α-glucosidase inhibitory activity.

These compounds inhibit α-glucosidase localized on the intestinal epithelium and suppress decomposition of a saccharide to suppress and/or delay absorption, thereby suppressing elevation of blood sugar level. Furthermore, since these compounds each are a catechin (EGCG) polymer contained in oolong tea, they are excellent in flavor and safety and can take for a long time. From these findings, they found that it is possible to provide a food and drink for suppressing absorption of sugar derived from a meal and preventing and/or treating diabetes caused by chronic hyperglycemia for a long time by adding an α-glucosidase inhibitor to a food and drink, etc. Based on the finding, the present invention was accomplished.

More specifically, the present invention provides a novel compound of Formula 1 or Formula 2:

[Chem. 1]

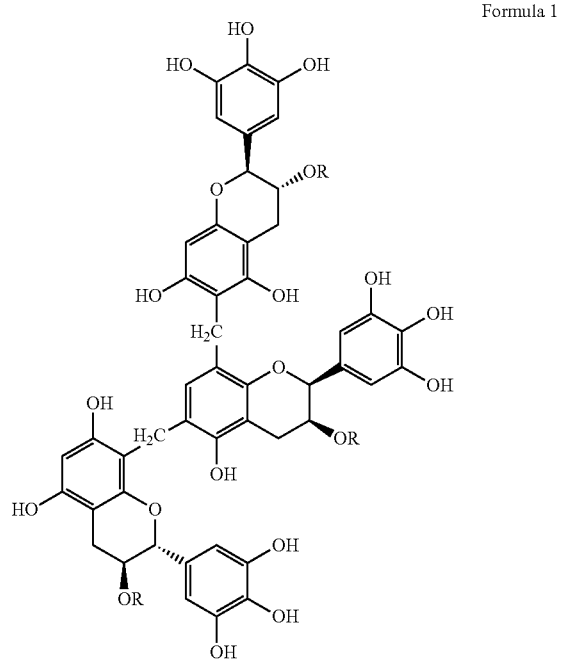

Formula 1

[Chem. 2]

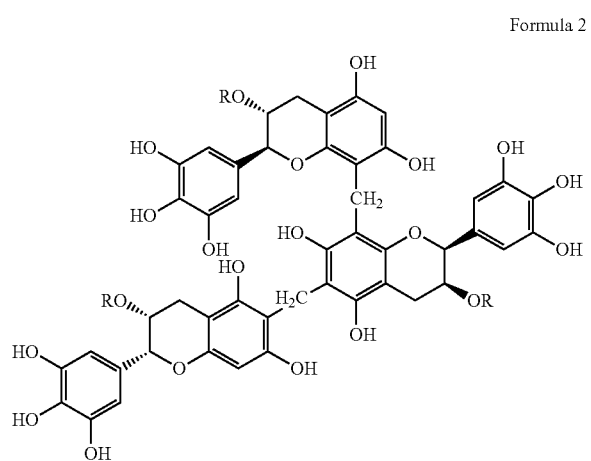

Formula 2 wherein R is galloyl or H, or a salt thereof.

The present invention further provides a food and drink or a pharmaceutical composition containing the compound of Formula 1 or 2 or a salt thereof.

The present invention also provides an α-glucosidase inhibitor containing an EGCG dimer, trimer and/or tetramer as an active ingredient. In addition, the present invention provides α-glucosidase inhibitor containing an EGCG trimer and/or tetramer as an active ingredient.

The present invention also provides an α-glucosidase inhibitor containing an EGCG dimer, trimer and/or tetramer as an active ingredient, in which the EGCG dimer is theasinensin-D and/or oolong homobisflavan-A; the EGCG trimer is at least one selected from oolong homobisflavan-trimer-1, oolong homobisflavan-trimer-2 and oolong homobisflavan-trimer-4; and the EGCG tetramer is oolong homobisflavan-tetramer-1 and/or oolong homobisflavan-tetramer-2. In addition, the present invention provides an α-glucosidase inhibitor containing an EGCG trimer or tetramer as an active ingredient, in which the EGCG trimer is oolong homobisflavan-trimer-4 and the EGCG tetramer is oolong homobisflavan-tetramer-1.

The present invention further provides a composition for suppressing elevation of blood sugar level or an agent for preventing and/or treating diabetes which the α-glucosidase inhibitor mentioned above is added.

Advantageous Effects of Invention

The present invention provides an α-glucosidase inhibitor containing a novel epigallocatechin gallate trimer and epigallocatechin gallate polymer. The α-glucosidase inhibitor inhibits α-glucosidase localized on the intestinal epithelium and suppresses decomposition of a saccharide to suppress and/or delay absorption, thereby suppressing elevation of blood sugar level. Therefore, it is possible to provide a food and drink for suppressing absorption of sugar derived from a meal and preventing and/or treating diabetes caused by chronic hyperglycemia for a long time by adding an α-glucosidase inhibitor to a food and drink, etc.

DESCRIPTION OF EMBODIMENTS

Novel Compound

Figure 1:
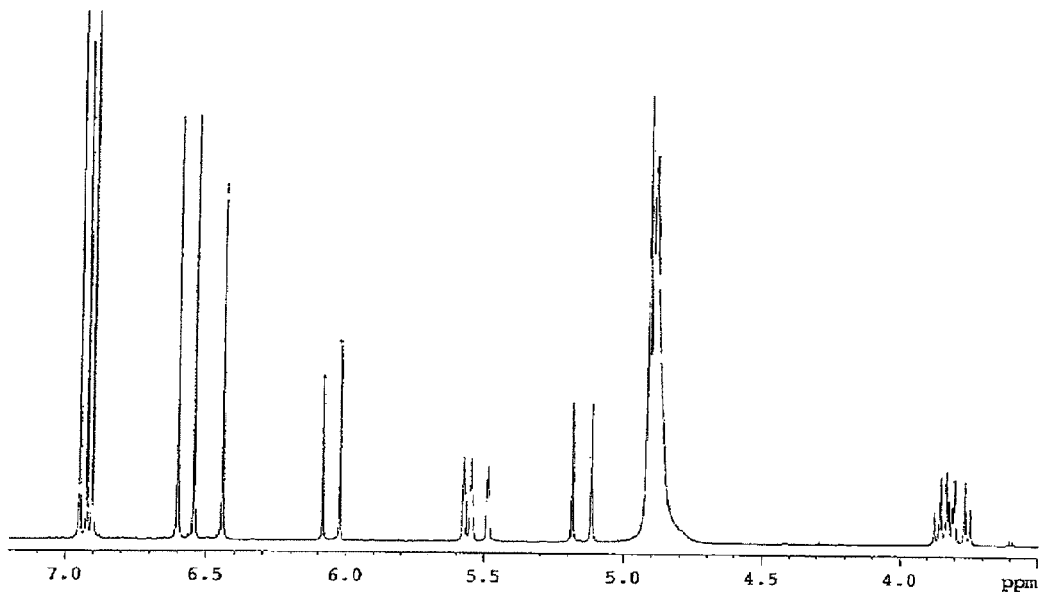
FIG. 1 shows a $^1$H NMR spectrum of compound 3.

The present invention relates to a novel compound of an EGCG trimer.

A compound of the present invention is a compound of Formula 1 or Formula 2:

[Chem. 3]

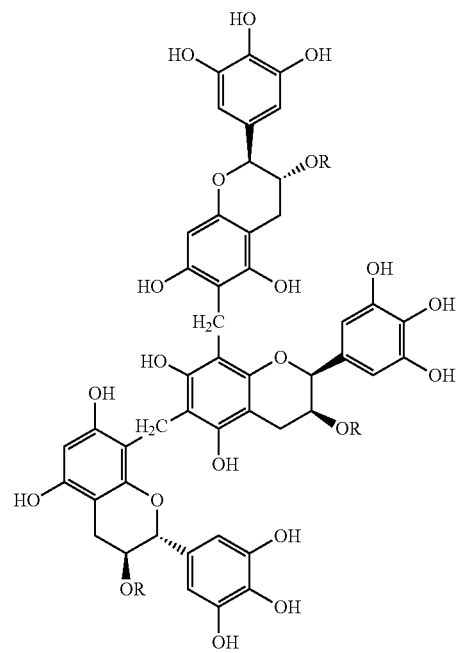

Formula 1

[Chem. 4]

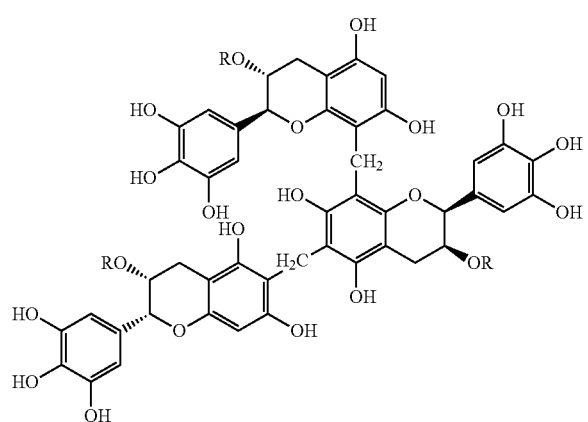

Formula 2 wherein R is galloyl or H, or a salt thereof.

The compound of Formula 1 or Formula 2 has asymmetric centers at position 2 and position 3 on a chroman ring as a constitutional unit.

The compound of Formula 1 can be expressed as EGCG6:8EGCG6:8EGCG based on a coupling scheme of a monomer, EGCG, and the compound of Formula 2 can be expressed as EGCG8:8EGCG6:6EGCG based on a coupling scheme of a monomer, EGCG.

A compound of Formula 1 wherein R is galloyl is an oolong homobisflavan-trimer-2 defined in the specification. Furthermore, a compound of Formula 2 wherein R is galloyl is an oolong homobisflavan-trimer-4 defined in the specification. The galloyl group can be removed by hydrolysis. Such hydrolysis can be performed by use of an aqueous solution of a basic compound such as sodium hydroxide, potassium hydroxide, sodium hydrogen carbonate and sodium carbonate or by use of a hydrolytic enzyme such as an enzyme having tannase activity. In such hydrolysis, 1, 2 or 3 gallate groups of three gallate groups are removed to provide a mixture of a plurality of compounds. In this case, individual compounds can be isolated from the mixture by use of a known purification method such as open column chromatography using a styrene based adsorption resin such as HP-20 (manufactured by Mitsubishi Chemical Corporation) and a dextran based resin such as Shephadex LH-20 (manufactured by Amersham Biosciences AB, Sweden) and high performance liquid chromatography (HPLC).

The present invention also relates to a salt of the compound of Formula 1 or Formula 2.

Such a salt is not particularly limited as long as it is a salt that can be formed from the compound of Formula 1 or 2; however, a pharmaceutically acceptable salt is preferable.

Examples thereof include a metal salt with a metal element belonging to the first or second family of the periodic table, such as a lithium salt, a sodium salt, a potassium salt, a calcium salt and a magnesium salt of a compound of Formula 1 or 2. Such a metal salt can be formed with, for example, a hydroxide group of the compound of Formula 1 or 2 (a phenolic hydroxide group, a hydroxide group in the case where either one or all of R is H).

For example, in a non-protic solvent, a compound of Formula 1 or 2 is reacted with metallic sodium or sodium hydride to convert a hydroxide group (—OH) into a sodium alkoxide group (—ONa) to thereby produce a sodium salt of the compound of Formula 1 or 2. Furthermore, all hydroxide groups contained in the compound of Formula 1 or 2 can be converted into sodium alkoxide groups or only part of the hydroxide groups can be converted into sodium alkoxide groups by controlling the amount of metallic sodium or sodium hydride used.

A compound represented by Formula 1 or 2 of the present invention can be produced as follows.

A compound where either one of R is a gallate group can be produced by reacting EGCG with formaldehyde in a solvent in the presence of an acid.

Examples of the solvent that can be used in the reaction include methanol and alcohols such as ethanol, n-propanol and iso-propanol. The amount of solvent used is not particularly limited; however, for example, 20 to 200 parts by mass of solvent can be used relative to 1 part by mass of EGCG.

Examples of the acid that can be used herein include mineral acids such as hydrochloric acid, sulfuric acid and nitric acid; and organic acids such as formic acid and acetic acid. The amount of acid used is not particularly limited; however, for example, 0.01 to 2 mole of acid can be used relative to 1 mole of EGCG.

In the case of formaldehyde, for example, 1 to 100 moles can be used relative to 1 mole of EGCG.

Reaction temperature and time may vary depending upon the amount of solvent, etc. For example, the reaction temperature is −10 to 50° C. and the reaction time is 0.2 to 12 hours. Typically, the reaction temperature is room temperature (about 25° C.).

The compound of Formula 1 or 2 wherein either one of R is H (hydrogen atom) can be produced by reacting (−)-epigallocatechin in place of (−)-epigallocatechin-3-O-gallate with formaldehyde in the same manner as above.

A product obtained by the reaction of (−)-epigallocatechin-3-O-gallate or (−)-epigallocatechin with formaldehyde is usually a mixture of chroman polymer compounds, which contains at least two types of compounds different in coupling scheme of a chroman ring by a methylene group. The compound of Formula 1 or 2 can be isolated from such a mixture by using a known purification method, for example, open column chromatography using a styrene based adsorption resin such as HP-20 (manufactured by Mitsubishi Chemical Corporation) and a dextran based resin such as Shephadex LH-20 (manufactured by Amersham Biosciences AB, Sweden) and high performance liquid chromatography (HPLC).

The compound of Formula 1 or 2 of the present invention is a novel compound; however, it was found to be present in oolong tea as described later in Examples. The compound of the present invention can be also isolated from teas using *Camellia sinensis* as a raw material and preferably from fermented tea such as oolong tea and black tea or roasted tea by extraction and purification.

Food and Drink and Pharmaceutical Composition Containing a Novel EGCG Trimer

The present invention relates to a food and drink or pharmaceutical composition containing at least one of a novel trimer or a salt thereof as mentioned above.

Examples of the beverage containing a compound of the present invention include refreshing drinks, tea drinks, liquid tonic medicines, healthy drinks, nutrition drinks, sports drinks and carbonated drinks (including concentrated stock solutions and preparatory powders of these beverages). Examples of the food include gums, candies, jellies, tablets, health foods, nutrition foods and supplements.

When a compound of the present invention is used as a medicinal drug such as a drug for preventing diabetes, the medicinal drug can be provided in the dosage form of powder, grain, tablet, capsule, liquid and injection. A compound of the present invention or a salt thereof can be orally administered directly or by diluting it with water or the like. Alternatively, it is formed into a preparation with a known carrier for a medicinal drug. For example, a compound of the present invention or a salt thereof can be administered as a peroral liquid preparation such as a syrup agent or a peroral solid preparation such as a tablet, a capsule, a grain, and a powder by processing it into an extract or a powder and blending it with a pharmaceutically acceptable carrier. Examples of the pharmaceutically acceptable carrier include organic or inorganic carrier substances conventionally used as a preparation material. The carrier is blended as an excipient, a lubricant, a binding agent and a disintegrator in a solid preparation and as e.g., a solvent, an excipient, a suspension agent and a binding agent in a liquid preparation. Furthermore, if necessary, additives for a preparation such as an antiseptic agent, an antioxidizer, a coloring agent and a sweetening agent can be also used.

In a food and drink or pharmaceutical composition containing a compound of the present invention, the compound of the present invention can be contained in any concentration. Preferably, at least one of the novel trimers or salts thereof, as a compound of the present invention, is contained in a total concentration of 0.18 to 20 µg/ml and more preferably 0.3 to 10 µg/ml.

Furthermore, an effective dose thereof can be appropriately determined depending upon the age and body weight of a patient, the type and significance of a disease and the administration route.

Alpha-Glucosidase Inhibitor Containing an EGCG Dimer, Trimer and/or Tetramer as an Active Ingredient The present invention provides an α-glucosidase inhibitor containing an EGCG polymer as an active ingredient. More specifically, an α-glucosidase inhibitor containing an EGCG dimer to tetramer as an active ingredient.

The EGCG polymer serving as an active ingredient, in particular, an EGCG dimer to tetramer, can be obtained by the aforementioned synthesis/purification method or by a separation/purification method from a naturally occurring substance.

The EGCG polymer is used as an inclusive term of compounds obtained by polymerization of EGCG in accordance with an arbitrary formula, include a compound of a dimer or more polymerized through a methylene group at the position 6 and/or 8 on a chroman ring, a compound of a dimer or more such as theasinensin A or theasinensin-D, polymerized in such a coupling scheme that positions 2' on B rings are mutually bonded by a C—C bond, and a compound of dimer or more such as oolongtheanin-gallate, polymerized in such a coupling scheme that B rings are condensed.

Examples of the EGCG dimer to tetramer include dimers such as theasinensin-D and oolong homobisflavan-B; trimers such as oolong homobisflavan-trimer-1, oolong homobisflavan-trimer-2 and oolong homobisflavan-trimer-4; and tetramers such as oolong homobisflavan-tetramer-1 and oolong homobisflavan-tetramer-2. Of them, particularly, oolong homobisflavan-trimer-4 and oolong homobisflavan-tetramer-1 have high activity.

In an α-glucosidase inhibitor of the present invention, an EGCG dimer to tetramer serving as an active ingredient can be contained in an arbitrary ratio. Preferably, the EGCG dimer to tetramer serving as an active ingredient is contained in a total concentration of 0.45 to 50 µg/ml and more preferably in a total concentration of 0.7 to 25 µg/ml.

Alternatively, the α-glucosidase inhibitor of the present invention contains a dimer, i.e., theasinensin-D and/or oolong homobisflavan-B in a concentration of 0.1 to 200 µg/ml and more preferably in a concentration of 0.25 to 120 µg/ml. Alternatively, the α-glucosidase inhibitor of the present invention contains a trimer, i.e., oolong homobisflavan-trimer-1, oolong homobisflavan-trimer-2 and/or oolong homobisflavan-trimer-4 in a concentration of 0.18 to 20 µg/ml and more preferably in a concentration of 0.3 to 10 µg/ml. Alternatively, the α-glucosidase inhibitor of the present invention contains a tetramer, i.e., oolong homobisflavan-tetramer-1 and/or oolong homobisflavan-tetramer-2 in a concentration of 0.06 to 20 µg/ml and more preferably in a concentration of 0.12 to 10 µg/ml.

The inhibitory activity of α-glucosidase can be measured by any one of the α-glucosidase activity evaluation methods described in prior applications set forth in the Background Art. Furthermore, the activity can be evaluated by the method shown in Example 2 described later. The inhibitory activity can be also expressed by $IC_{50}$, which is the amount of a sample inhibiting 50% of the enzymatic activity.

The α-glucosidase inhibitor of the present invention can suppress decomposition of starch derived from a meal and sugar derived from a polysaccharide in a dose lower than that of α-glucosidase derived from naturally occurring substance known in the art, thereby suppressing absorption. Furthermore, the compounds are all catechin (EGCG) polymers contained in oolong tea, etc., and thus excellent in flavor and safety and capable of being taken for a long time.

Composition for Suppressing Elevation of Blood Sugar Level or Agent for Preventing and/or Treating Diabetes which α-Glucosidase Inhibitor Having an EGCG Dimer, Trimer and/or Tetramer as an Active Ingredient is Added It is possible to provide a food and drink for suppressing absorption/suppression of a sugar derived from a meal and preventing and/or treating diabetes caused by chronic hyperglycemia for a long time by adding the α-glucosidase inhibitor of the present invention to a food and drink, etc.

The food and drink and pharmaceutical composition of the present invention can contain an EGCG dimer to tetramer as an active ingredient in an arbitrary ratio. Preferably, the food and drink and pharmaceutical composition contain the EGCG dimer to tetramer as an active ingredient in a total concentration of 0.45 to 50 μg/ml, more preferably 0.7 to 25 μg/ml and particularly preferably 0.7 to 10 μg/ml.

Alternatively, the food and drink and pharmaceutical composition of the present invention contain a dimer, i.e., theasinensin-D and/or oolong homobisflavan-B in a concentration of 0.1 to 200 μg/ml and more preferably 0.25 to 120 μg/ml. Alternatively, the food and drink and pharmaceutical composition of the present invention contain a trimer, i.e., oolong homobisflavan-trimer-1, oolong homobisflavan-trimer-2 and/or oolong homobisflavan-trimer-4 in a concentration of 0.18 to 20 μg/ml and more preferably 0.3 to 10 μg/ml. Alternatively, the food and drink and pharmaceutical composition of the present invention contain a tetramer, i.e., oolong homobisflavan-tetramer-1 and/or oolong homobisflavan-tetramer-2 in a concentration of 0.06 to 20 μg/ml and more preferably 0.12 to 10 μg/ml.

In the present invention, the amount of the active ingredient used varies depending upon the method for use; however, it is not particularly limited as long as the inhibitory action of α-glucosidase is exerted. For example, when a food and drink is prepared for suppressing elevation of blood sugar level and preventing and/or treating diabetes, the α-glucosidase inhibitor of the present invention can be blended such that the inhibitor of about 10 μg to 600 mg, preferably 50 μg to 100 mg, and more preferably 100 μg to 100 mg can be taken per day.

The present invention will be more specifically described by way of Examples; however, the present invention is not limited by these.

EXAMPLE 1

Synthesis and Purification of EGCG Polymer

A. Synthesis and Fractionation by Open Column:

Six grams of EGCG (Teavigo (registered trade mark) manufactured by Roche) was dissolved in 120 ml of ethanol containing 0.02N HCl, and a 4% formaldehyde ethanol solution (180 ml) was added and then, stirred at room temperature for 4 hours. After completion of the reaction, the resultant reaction solution was diluted 10 fold with pure water and loaded on an adsorption resin CHP-20P column (600 ml, 37-75 μm, manufactured by Mitsubishi Chemical Corporation). After washed with water (1200 ml), elution was performed sequentially with 900 ml of 25% $CH_3CN$ and 1200 ml of 30% $CH_3CN$. The elution fraction with 25% $CH_3CN$ was separated into three fractions (fr. 1 to fr. 3) of 300 ml for each, whereas the elution fraction with 30% $CH_3CN$ was separated into four fractions (fr. 4 to fr. 7) of 300 ml for each.

B. Preparative HPLC Conditions:

The fractionated products obtained by the CHP-20P column purification was further purified by reverse-phase preparative HPLC.
<Conditions>
Column: Develosil ODS-HG-5 (5 cm φ×50 cm, manufactured by Nomura Chemical Co., Ltd.)
Mobile phase: A: 0.05% $TFA/H_2O$, B: 90% $CH_3CN$, 0.05% $TFA/H_2O$, 32 ml/min
Gradient program: B 20% isocratic (30 min), a 100 min linear gradient from B 20% to B 40%, B 40% isocratic (20 min)

Detection: A280 nm
Sample: fr. 2 to fr. 7 obtained by CHP-20P column purification each were dissolved in 20% $CH_3CN$ and the total amount was loaded by several times.

In the above analysis conditions, individual peaks corresponding to retention time 109 minutes (compound 1), 113 minutes (compound 2), 120 minutes (compound 3), 130 minutes (compound 4), 85 minutes (compound 5), 106 minutes (compound 6) and retention time 104 minutes (compound 7) were collected.

C. Structural Analysis of Compound:

The compounds isolated by preparative HPLC were subjected to MS and NMR measurements. Of them, MS of compounds 5 to 7 were measured by Q-TOF Premier (manufactured by Micromass, UK) in a negative, V mode. As a result, ion peaks thereof were observed respectively at m/z 927.160, 927.163, and 1397.248 $[M-H]^-$. Furthermore, NMR spectrum data of compound 5 coincided with the NMR spectrum data of oolong homobisflavan-A described in the literature (Chem. Pharm. Bull 37(12), 3255-3563 (1989)). The NMR spectrum data of compound 6 coincided with the NMR spectrum data of oolong homobisflavan-B described in the literature (Chem. Pharm. Bull 37(12), 3255-3563 (1989)). Furthermore, The NMR spectrum data of compound 7 coincided with the NMR spectrum of an epigallocatechin trimer (oolong homobisflavan-trimer-1) described as a compound (4) of Patent Application (WO2005/116005), paragraph No. 0029. From these results, compound 5 was identified as oolong homobisflavan-A represented by Formula 3, compound 6 as oolong homobisflavan-B represented by Formula 4 and compound 7 as oolong homobisflavan-trimer-1 represented by Formula 5.

[Chem. 5]

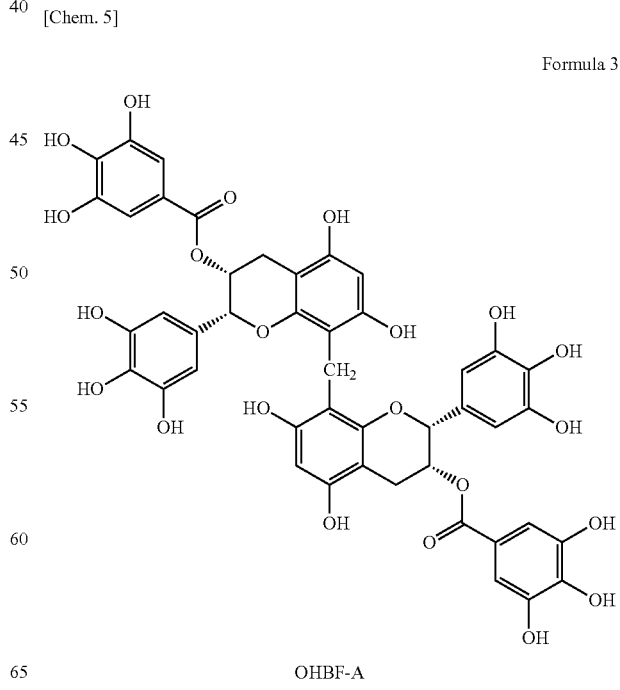

Formula 3

OHBF-A

[Chem. 6]

Formula 6

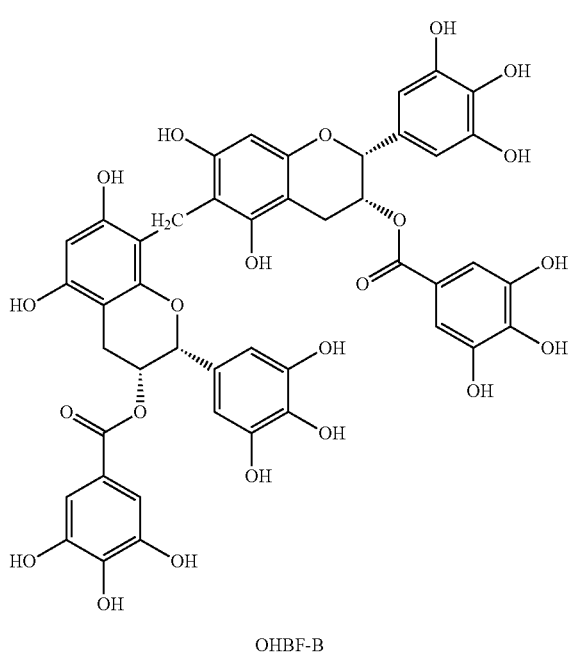

OHBF-B

[Chem. 7]

Formula 5

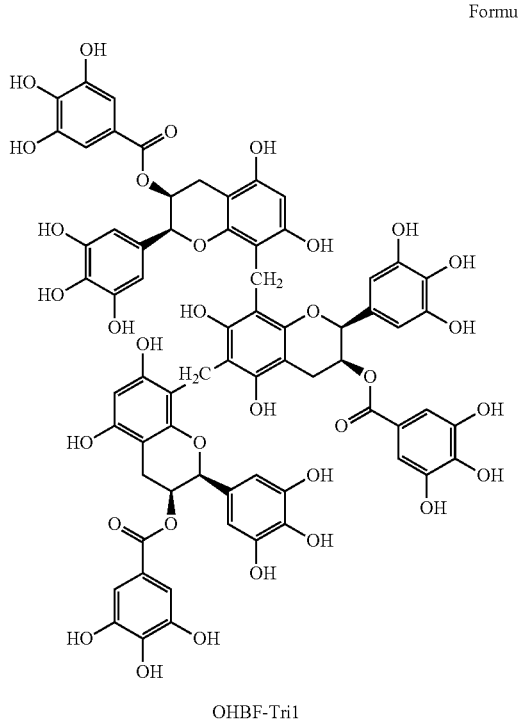

OHBF-Tri1

Compound 1 to compound 4 were subjected to structural analysis by the following MS and NMR. MS measurement was performed by Q-TOF Premier (manufactured by Micromass, UK) using ESI having a Z spray ion source as an ion source in a negative, V mode. Mass correction was performed by lock spray at a Cone voltage: 45 V, Capillary voltage: 3 KV, and Desolvation Temp.: 180° C. As a reference, leucine enkephalin (m/z 554.2615 [M−H]$^-$) was used.

As a result, compound 3 gave molecular ions of m/z 1397.2479 [M−H]$^-$ and a molecular formula thereof was calculated as $C_{68}H_{54}O_{33}$ (err.: 0.7 ppm); compound 4 gage molecular ions of m/z 1397.2509[M−H]$^-$ and a molecular formula thereof was calculated as $C_{68}H_{54}O_{33}$ (err.: 2.9 ppm). They were estimated as substances having three EGCG molecules are crosslinked with two methylene groups. Furthermore, compound 1 gave molecular ions of m/z 1867.3112 [M−H]$^-$ and divalent 933.1517 [M−2H]$^{2-}$ and a molecular formula thereof was calculated as $C_{91}H_{72}O_{44}$ (err.: −11.0 ppm), and compound 2 gave molecular ions of m/z 1867.3100 [M−H]$^-$ and divalent 933.1151 [M−2H]$^{2-}$ and a molecular formula thereof was calculated as $C_{91}H_{72}O_{44}$ (err.: −11.7 ppm) and were estimated as substances having four EGCG molecules crosslinked with three methylenes.

Figure 2:
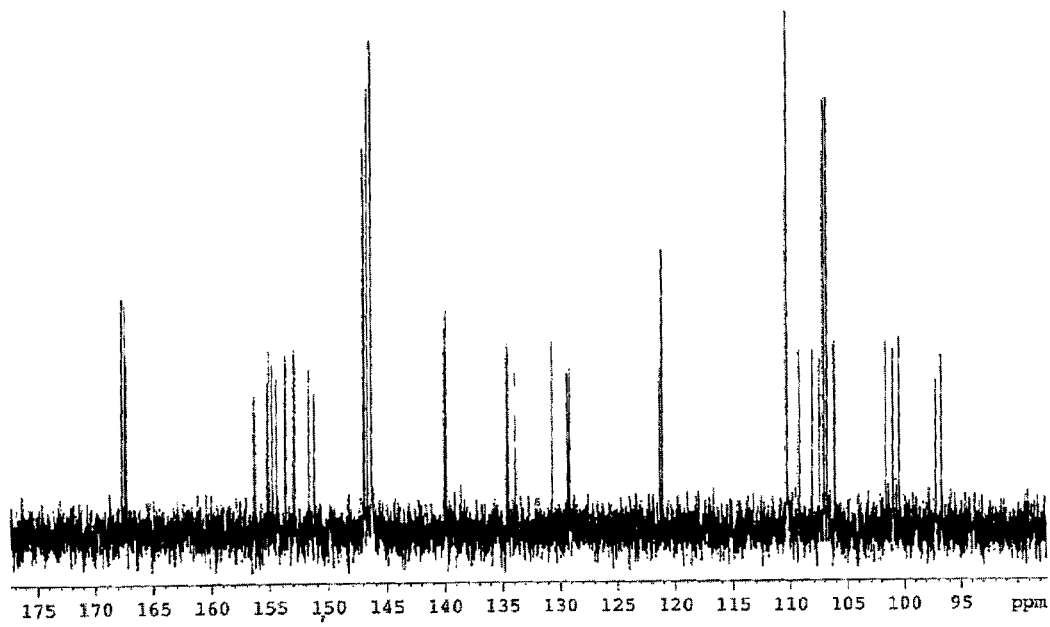
FIG. 2 shows a $^{13}$C NMR spectrum of compound 3.
Figure 3:
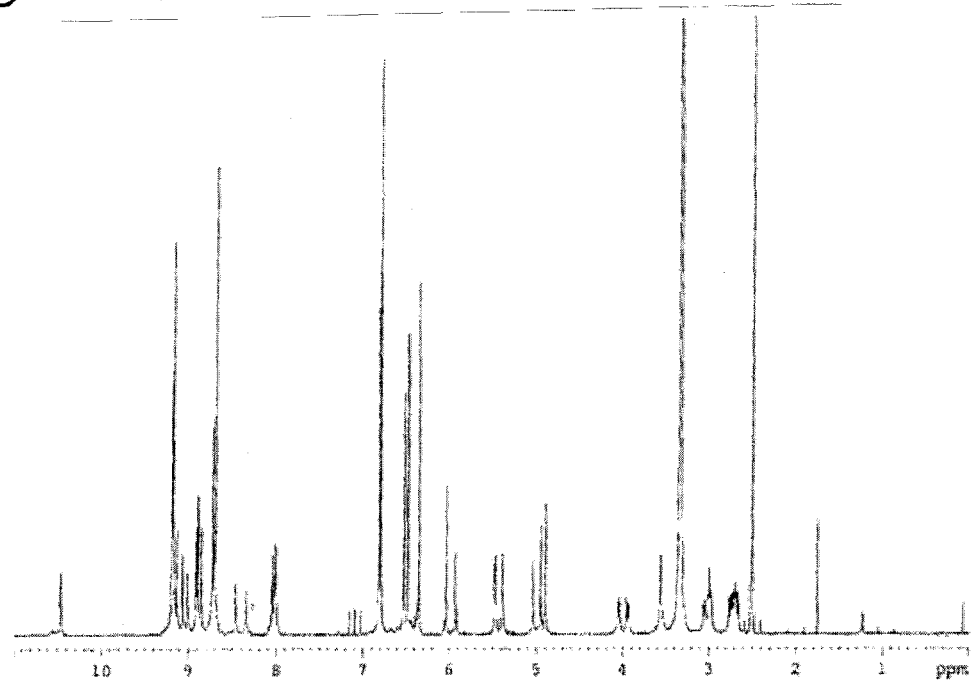
FIG. 3 shows a $^1$H NMR spectrum of compound 4.
Figure 4:
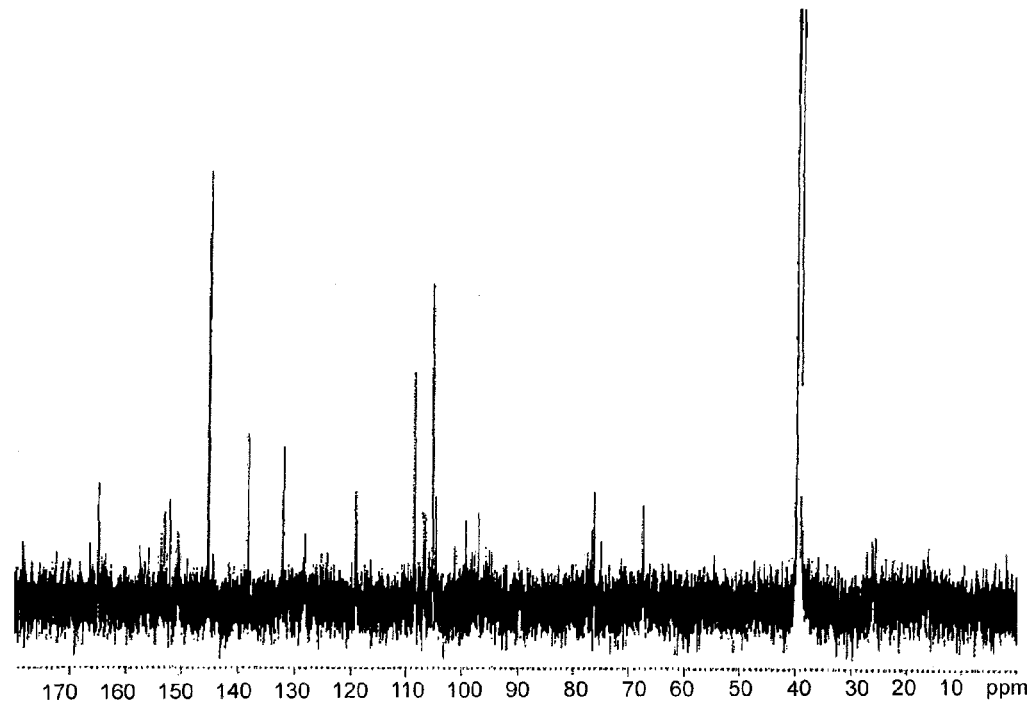
FIG. 4 shows a $^{13}$C NMR spectrum of compound 4.
Figure 9:
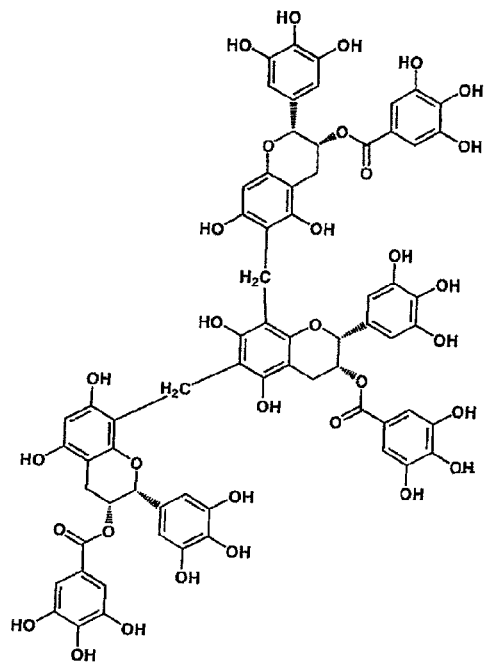
FIG. 9 shows the structure of oolong homobisflavan-trimer-2.
Figure 10:
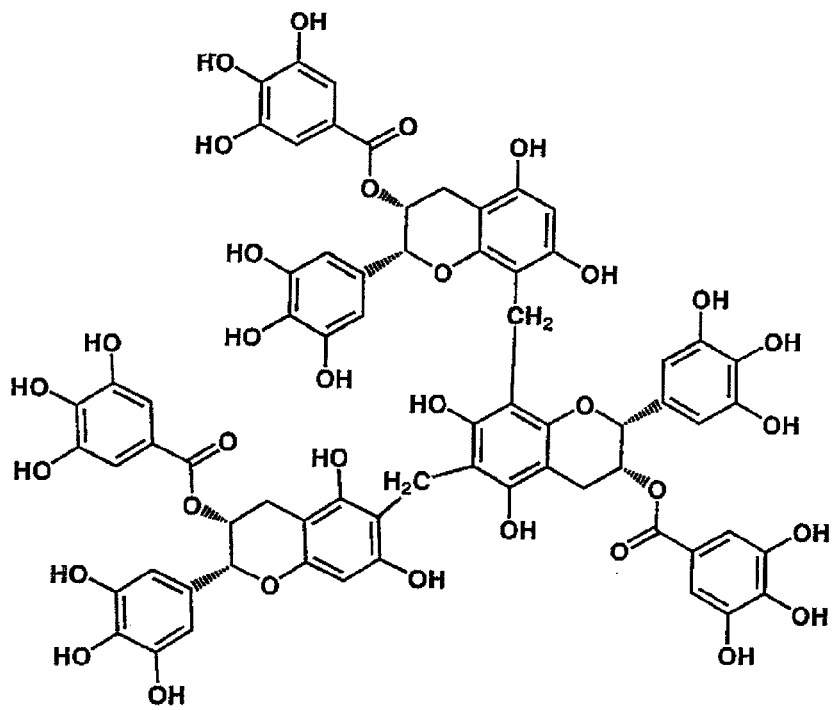
FIG. 10 shows the structure of oolong homobisflavan-trimer-4.

NMR was measured in the following conditions. Compound 3 was dissolved in $CD_3OH$ and compound 4 was dissolved in DMSO-d6 (($CD_3)_2SO$). These were used as measurement samples. Residual peaks of a proton of $CD_3OH$ and $^{13}C$, i.e., δ3.30 and δ48.97 were used as the internal standards of compound 3. Residual peaks of $^1H$ of DMSO-d6, i.e., 2.50 ppm and $^{13}C$, i.e., δ39.43 were used as the internal standards of compound 4. Measurement items, which were $^1H$ NMR, $^{13}C$ NMR, $^1H\{^{13}C\}$-HSQC, $^1H\{^{13}C\}$-HMBC, TOCSY and DQF-COSY, were measured by DMX-750 spectrometer (BRUKER BIOSPIN, Germany). As a result of the NMR, it was elucidated that compound 3 is a compound bonded in the scheme of EGCG6:8EGCG6:8EGCG (oolong homobisflavan-trimer-2) and compound 4 is a compound bonded in the scheme of EGCG8:8EGCG6:6EGCG (oolong homobisflavan-trimer-4). The bond between EGCG molecules represented by 6:8 or 8:8 expresses that the carbon at position 6 or 8 on EGCG A ring is crosslinked with a counterpart via a methylene group sandwiched between them. The $^1H$ NMR and $^{13}C$ NMR spectra of compound 3 are shown in FIGS. 1 and 2. The $^1H$ NMR and $^{13}C$ NMR spectra of compound 4 are shown in FIGS. 3 and 4. The structure of compound 3 is shown in FIG. 9 and the structure of compound 4 is shown in FIG. 10.

Compound 3:

With respect to oolong homobisflavan-trimer-2 (in $CD_3OH$), signals of $^1H$ NMR observed were δ 6.95, 6.92, 6.90, 6.60, 6.54, 6.44, 6.08, 6.02, 5.57, 5.55, 5.49, 5.18, 5.12, 4.91, 3.86, 3.83, 3.81, 3.76, 3.03, 3.01, 2.94, 2.89, 2.89, 2.82, and signals of $^{13}C$ NMR observed were δ 167.72, 167.46, 167.37, 156.29, 155.25, 155.08, 154.79, 154.43, 153.64, 152.91, 151.64, 151.20, 147.00, 146.93, 146.38, 146.38, 146.34, 146.29, 140.03, 139.89, 139.89, 134.65, 134.48, 133.85, 130.64, 129.29, 129.10, 121.33, 121.14, 121.14, 110.31, 110.24, 110.24, 109.19, 108.07, 107.42, 107.05, 107.02, 106.79, 106.10, 101.59, 101.00, 100.45, 97.23, 96.71, 80.07, 79.94, 78.45, 70.00, 69.32, 69.28, 27.21, 27.21, 26.81, 17.91, 17.91.

Compound 4:

With respect to oolong homobisflavan-trimer-4 (in DMSO-d6) signals of $^1H$ NMR observed were δ 10.46, 9.18, 9.16, 9.16, 9.12, 9.06, 9.05, 8.90, 8.88, 8.84,8.72, 8.69, 8.69, 8.46, 8.34, 8.05, 8.02, 8.00, 6.81, 6.78, 6.78, 6.52, 6.47, 6.35, 6.03, 5.93, 5.48, 5.46, 5.39, 5.04, 4.95, 4.89, 4.05, 3.95, 3.56, 3.56, 3.06, 3.00, 2.98, 2.76, 2.71, 2.67 and signals of $^{13}C$ NMR observed were δ 165.11, 165.09, 164.99, 157.66, 154.29, 153.82, 153.48, 153.07, 152.68, 152.23, 152.18, 150.88, 145.56, 145.52, 145.50, 145.26, 145.24, 145.23, 138.43, 138.43, 138.39, 132.34, 132.23, 132.19, 128.34, 128.34, 128.23, 119.17, 119.12, 119.04, 110.35, 110.31, 110.29, 109.19, 108.59, 108.56, 108.51, 106.97, 106.63, 105.26, 105.26, 105.13, 104.73, 101.28, 99.44, 99.41, 98.21, 97.34, 97.15, 96.03, 79.48, 79.07, 78.47, 69.95, 69.39, 69.28, 27.18, 26.98, 26.58, 18.16, 17.13.

Furthermore, compound 1 and compound 2 were dissolved in DMSO-d6 and subjected to NMR measurement using residual peaks of $^1$H and $^{13}$C, i.e., δ2.50 and δ39.43 as the internal standards.

Figure 5:
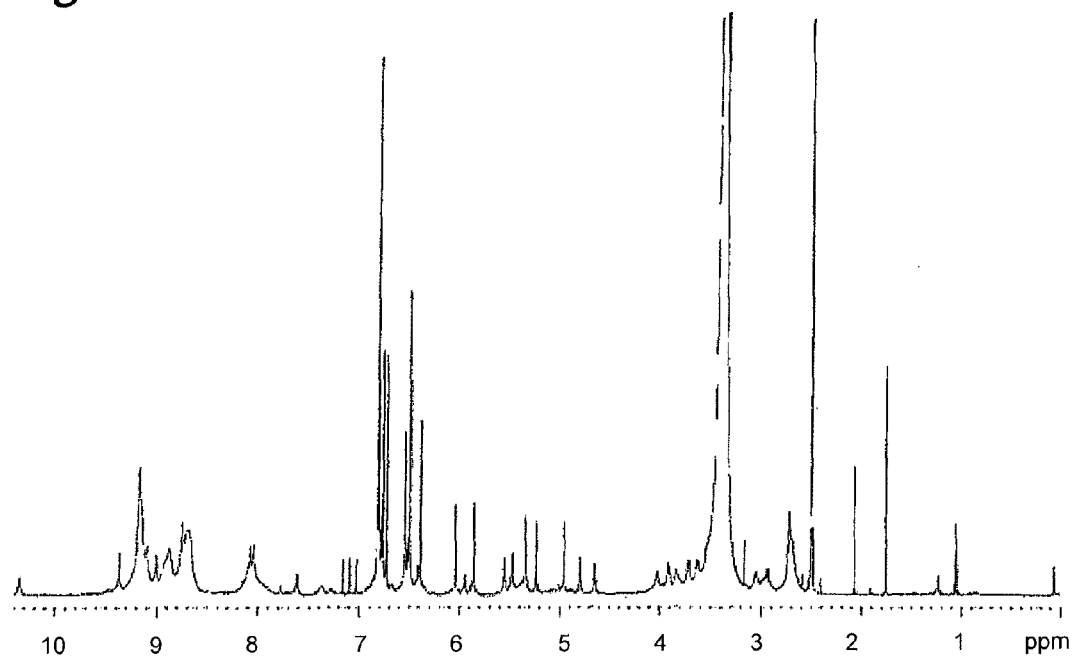
FIG. 5 shows a $^1$H NMR spectrum of compound 1.
Figure 6:
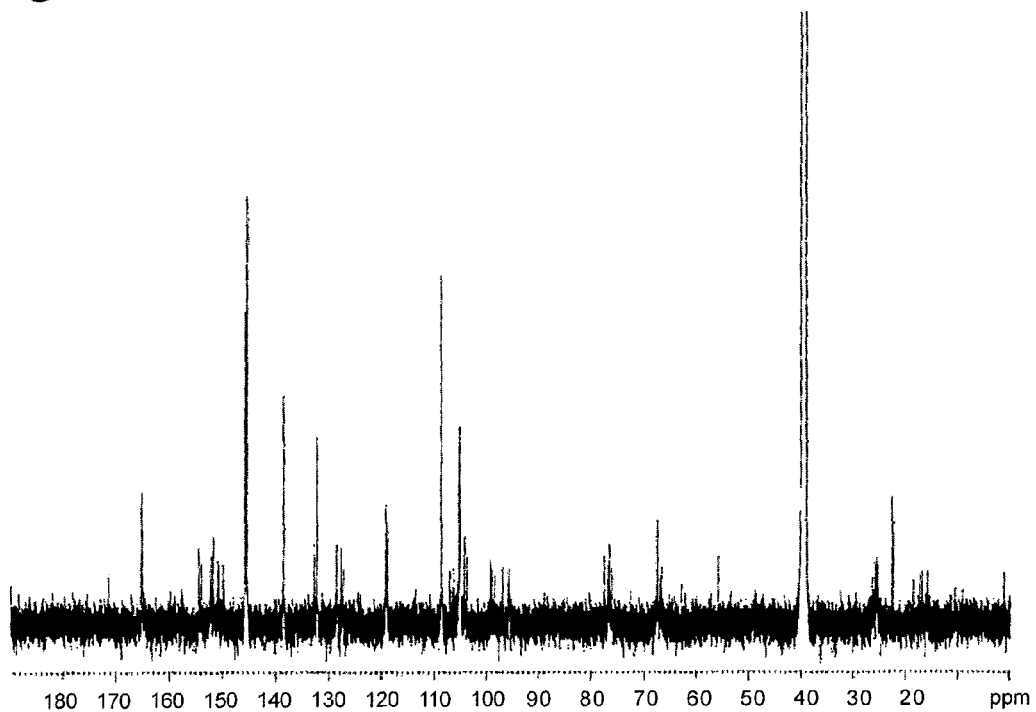
FIG. 6 shows a $^{13}$C NMR spectrum of compound 1.
Figure 7:
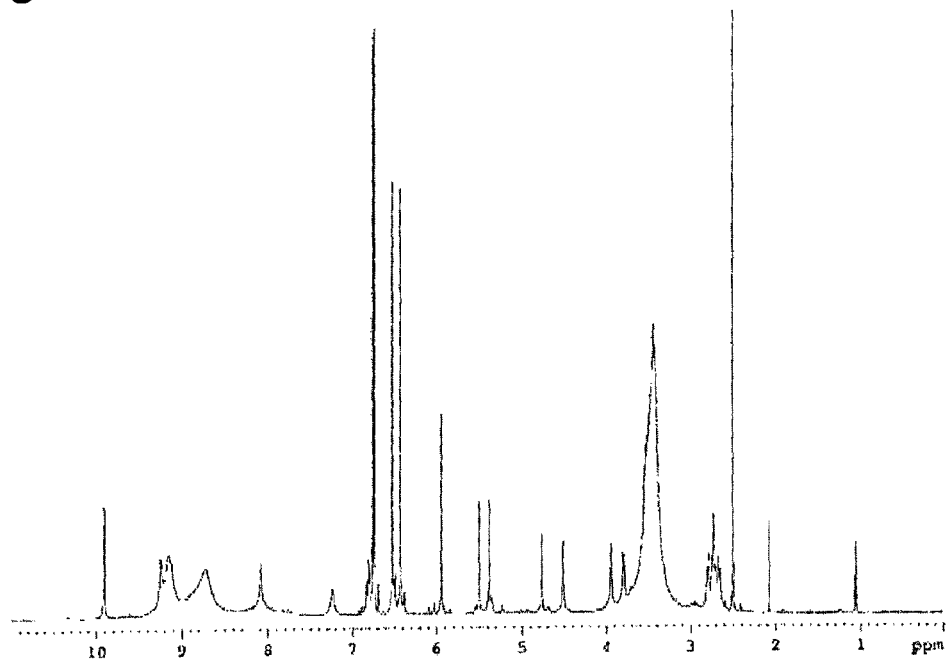
FIG. 7 shows a $^1$H NMR spectrum of compound 2.
Figure 8:
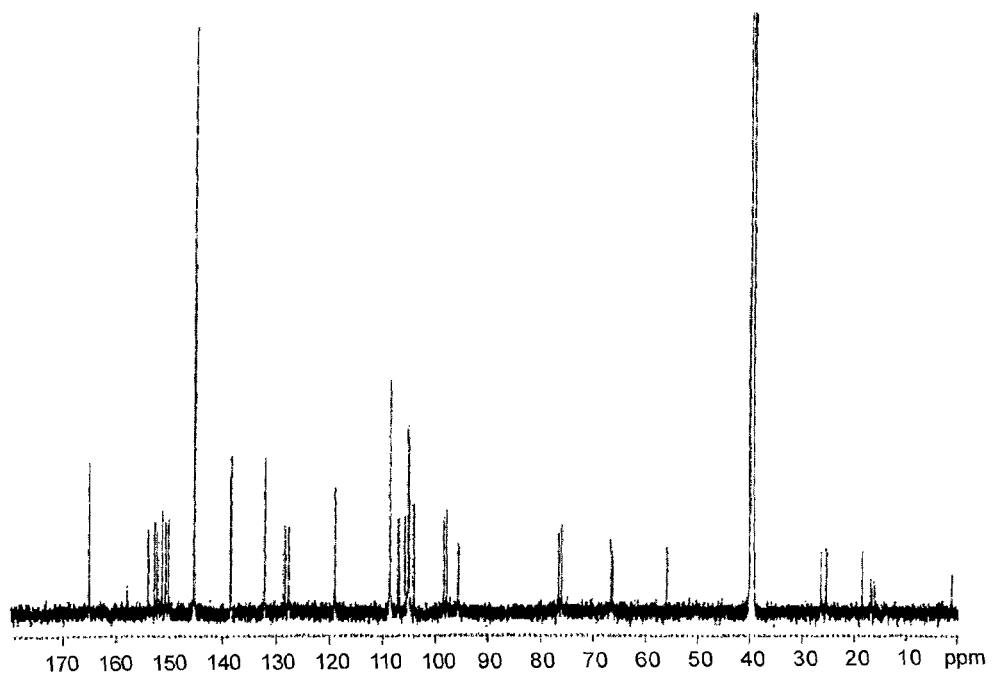
FIG. 8 shows a $^{13}$C NMR spectrum of compound 2.
Figure 11:
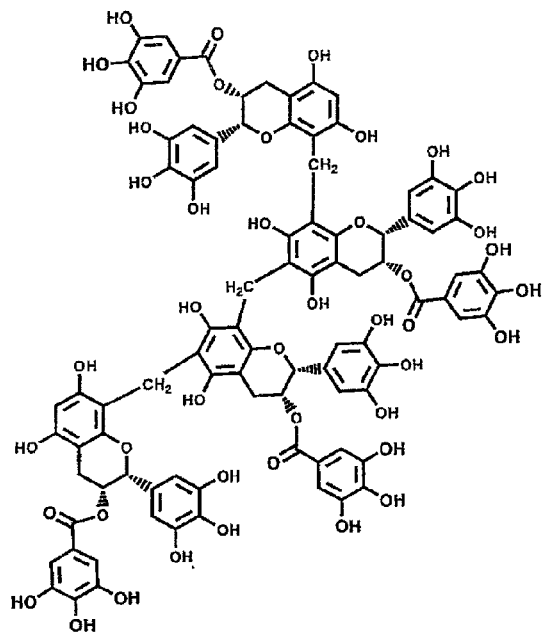
FIG. 11 shows the structure of oolong homobisflavan-tetramer-1.
Figure 12:
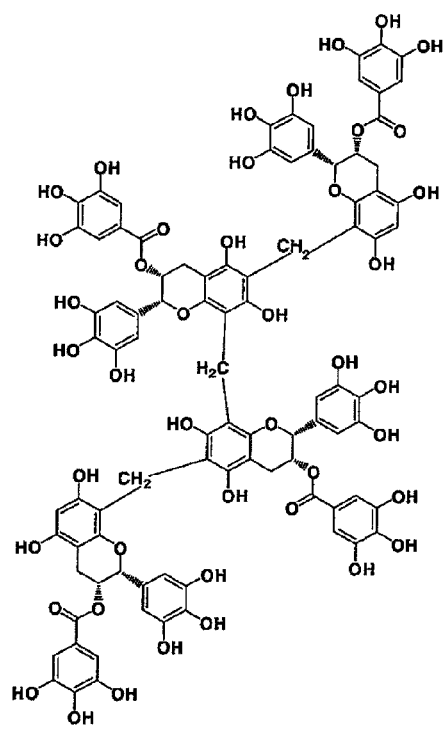
FIG. 12 shows the structure of oolong homobisflavan-tetramer-2.

Measurement items, which were $^1$H NMR, $^{13}$C NMR, $^1$H{$^{13}$C}-HSQC, $^1$H{$^{13}$C}-HMBC, TOCSY and DQF-COSY, were measured by DMX-750 spectrometer (BRUKER BIOSPIN, Germany). As a result of NMR, it was elucidated that compound 1 is a compound bonded in the scheme of EGCG8:8EGCG6:8EGCG6:8EGCG (oolong homobisflavan-tetramer-1), and compound 2 is a compound bonded in the scheme of EGCG8:6EGCG8:8EGCG6:8EGCG (oolong homobisflavan-tetramer-2). The bond between EGCG molecules represented by 6:8 or 8:8 expresses that the carbon at position 6 or 8 on EGCG A ring is crosslinked with a counterpart via a methylene group sandwiched between them. The $^1$H NMR and $^{13}$C NMR spectra of compound 1 are shown in FIGS. 5 and 6. The $^1$H NMR and $^{13}$C NMR spectra of compound 2 are shown in FIGS. 7 and 8. The structure of compound 1 is shown in FIG. 11 and the structure of compound 2 is shown in FIG. 12.

Compound 1:

With respect to oolong homobisflavan-tetramer-1, signals of $^1$H NMR (in DMSO-d6) observed were δ 10.34, 9.37, 9.17, 9.09, 9.01, 8.88, 8.75, 8.71, 8.68, 8.08, 8.04, 7.62, 6.81, 6.77, 6.72, 6.55, 6.49, 6.39, 6.04, 5.86, 5.55, 5.47, 5.34, 5.23, 4.96, 4.79, 4.64, 4.04, 4.02, 3.92, 3.90, 3.85, 3.83, 3.73, 3.71, 3.64, 3.62, 3.54, 3.52, 3.07, 3.05, 2.96, 2.93, 2.74, 2.72, 2.70 and signals of $^{13}$C NMR observed were δ 165.29, 165.13, 165.02, 165.01, 154.45, 154.44, 154.25, 152.33, 152.20, 151.97, 151.66, 151.62, 150.82, 150.66, 150.52, 149.66, 145.63, 145.56, 145.54, 145.50, 145.50, 145.27, 145.23, 145.18, 138.46, 138.38, 132.77, 132.26, 132.12, 128.50, 127.61, 119.20, 119.17, 118.96, 118.90, 108.73, 108.55, 107.05, 106.19, 105.19, 105.05, 104.31, 103.77, 99.01, 98.52, 77.44, 76.65, 76.51, 76.10, 67.53, 67.50, 66.95, 66.63, 25.94, 25.63, 25.49, 25.30, 17.14, 16.74, 15.81.

Compound 2:

With respect to oolong homobisflavan-tetramer-2, signals of $^1$H NMR (in DMSO-d6) observed were δ 9.91, 9.25, 9.16, 8.09, 7.22, 6.81, 6.76, 6.74, 6.52, 5.94, 5.50, 5.38, 4.77, 4.52, 3.95, 3.95, 3.80, 3.54, 2.80, 2.74, 2.73, 2.67 and signals of $^{13}$C NMR observed were δ 165.08, 165.01, 154.06, 152.83, 152.35, 151.45, 150.78, 150.26, 145.52, 145.52, 145.24, 145.18, 138.49, 138.44, 132.21, 132.10, 128.42, 127.63, 119.05, 118.95, 108.58, 108.46, 108.46, 106.95, 105.74, 104.92, 104.06, 98.32, 97.81, 76.59, 75.94, 66.69, 66.35, 26.33, 25.26, 16.72, 15.99.

Structural formulas of the individual compounds identified as mentioned above are shown in FIGS. 9 to 12. Oolong homobisflavan-trimer-2 is shown in FIG. 9, oolong homobisflavan-trimer-4 in FIG. 10, oolong homobisflavan-tetramer-1 in FIG. 11 and oolong homobisflavan-tetramer-2 in FIG. 12.

The yields of the individual compounds obtained by the aforementioned synthesis and purification were as follows: oolong homobisflavan-A (984 mg), oolong homobisflavan-B (374 mg), oolong homobisflavan-trimer-1 (468 mg), oolong homobisflavan-trimer-2 (73 mg), oolong homobisflavan-trimer-4 (12 mg), oolong homobisflavan-tetramer-1 (15 mg) and oolong homobisflavan-tetramer-2 (44 mg).

EXAMPLE 2

Alpa-Glucosidase Inhibitory Activity of EGCG Polymers

A 1M sodium phosphate buffer solution was prepared by blending 0.1 M NaH$_2$PO4.2H$_2$O and 0.1M Na$_2$HPO$_4$.12H$_2$O and the pH was adjusted to 7.0. To this, 2 g/L bovine serum albumin (F-V, manufactured by Nacalai Tesque Inc., pH 5.2, purity 96%) and 0.2 g/L NaN$_3$ (manufactured by Nacalai Tesque Inc., special grade reagent) were added. An enzyme solution was prepared by dissolving α-glucosidase (manufactured by Wako Pure Chemical Industries Ltd., derived from yeast, 100 units/mg) in the above buffer solution so as to obtain 0.5 units/mg protein /ml (100 μg/20 ml). A substrate solution was prepared by dissolving p-nitrophenyl-α-D-glucopyranoside (manufactured by Nacalai Tesque Inc., special grade reagent) in the buffer solution so as to obtain 5 mM (7.525 mg/5 ml).

Of the samples used for evaluation, theasinensin (TSN)-A and TSN-D were synthesized in accordance with the paper (Hashimoto, F. Nonaka, G. Nishioka, I. Chem. Pharm. Bull. 36 (5), 1676-1684 (1988)) and oolongtheanin-gallate (hereinafter referred to as "OTNG") were synthesized in accordance with the method described in the paper of J. Agric. Food Chem. 53, 4593-4598 (2005). Epigallocatechin-3-O-gallate (EGCG) used herein was the one manufactured by Wako Pure Chemical Industries Ltd, 1-deoxynojirimycin hydrochloride used herein was the one manufactured by Sigma-Aldrich, theaflavins used herein were a mixture of theaflavins (i.e., theaflavin, theaflavin-3-gallate, theaflavin-3'-gallate and theaflavin-3,3'-digallate) manufactured by Kurita Water Industries Ltd. Furthermore, oolong homobisflavan-A, oolong homobisflavan-B, oolong homobisflavan-trimer-1, oolong homobisflavan-trimer-2, oolong homobisflavan-trimer-4, oolong homobisflavan-tetramer-1 and oolong homobisflavan-tetramer-2 used herein were those synthesized and purified in Example 1.

These samples were prepared so as to satisfy 10 mg/ml DMSO and serially diluted 6 times by doubling dilution. Using a 96-well microplate, enzyme solution (45 μL) was added to a sample solution (10 μL) and pre-incubated at 37° C. for 5 minutes. Thereafter, the substrate solution (45 μL) was added and absorbance was measured at A 405 nm. After incubation was performed at 37° C. for 5 minutes, absorbance was measured at A 405 nm. The inhibition rate was calculated as a difference from the absorbance at A405 nm of a control, which contains DMSO alone in place of a sample. Each activity measurement was performed twice.

As a result, the α-glucosidase inhibitory activity of each compound is expressed by an IC$_{50}$ value as shown in Table 1. Oolong homobisflavan-tetramer-1 and oolong homobisflavan-trimer-4 showed particularly strong activities.

TABLE 1

Alpha-glucosidase inhibitory activity of EGCG polymers

| | IC50 (mA) |
|---|---|
| OHBF-trimer-1 | 0.462 |
| OHBF-trimer-2 | 0.286 |
| OHBF-trimer-4 | 0.124 |
| OHBF-tetramer-1 | 0.075 |
| OHBF-tetramer-2 | 0.278 |
| TSN-D | 0.297 |
| OTNG | 0.601 |
| OHBF-A | 0.862 |
| OHBF-B | 0.331 |
| EGCG | 1.27 |
| Theaflavins | 0.389 |
| TSN-A | 0.599 |
| 1-Deoxynojirimycin | 0.461 |

EXAMPLE 3

Quantification of Polymerized Polyphenol by LC-MS/MS LC-MS/MS Measurement Conditions for Trimer and Tetramer and Quantification of Suntory Black Oolong Tea LC-MS/MS of an EGCG polymer was measured by 4000 Q TRAP (manufactured by Applied) using a turbo ion spray in the following conditions: Collision energy: 46 eV (nega.), Ionspray voltage: 4500V, Temp.: 450° C.

As a measurement channel for each compound in MRM (multiple reaction monitoring), 698.40/168.90 (nega. divalent) was used for oolong homobisflavan-trimers and oolong homobisflavan-trimer-1 was used as a standard substance. A channel of 933.16/168.90 (nega. divalent) was used for oolong homobisflavan-tetramers and oolong homobisflavan-tetramer-2 was used as a standard substance. Measurement was carried out in the following conditions.
Column: Develosil C30-UG-3 (manufactured by Nomura Chemical Co., Ltd., 3 mmφ×150 mm)
Flow rate: 0.3 ml/min, Column Temp.: 40° C.
Mobile phase A: 0.1% HCOOH/$H_2O$, Mobile phase B: 0.1% HCOOH/$CH_3CN$
Gradient program: B 9% (0 min)→B 60% (17 min)→B 85% (17.1 min), B 85% (17.1-19 min)

Since these compounds were contained only in a trace amount in black oolong tea, it was impossible to directly quantify them. Then, a solution of a black oolong tea blend (solution before sterilized) was fractionated stepwise by a CHP-20P column (manufactured by Mitsubishi Chemical Corporation). After each of the fractions was quantified, the concentrations of individual fractions detected were added up to obtain the concentration in the tea solution. The concentration in black oolong tea was obtained as follows. The concentration of trimers was obtained by converting the concentrations of five trimers detected in terms of oolong homobisflavan-trimer-1 and adding them up. It was 172 ng/ml. The concentration of tetramers was obtained by adding up the concentrations of four components detected. It was 55 ng/ml in terms of oolong homobisflavan-tetramer-2.

The invention claimed is:

1. A method for inhibiting α-glucosidase, comprising administering an epigallocatechin gallate dimer, trimer andor tetramer as an active ingredient.

2. The method according to claim 1, wherein the active ingredient is the epigallocatechin gallate trimer andor tenamer.

3. The method according to claim 1, wherein the epigallocatechin gallate dimer is theasinensin-D andor oolong homobisfiavan-B; the epigallocatechin gallate trimer is at least one selected from oolong homobisflavan-trimer-1, oolong homobisflavan-trimer-2and oolong homobisflavan-trimer-4; and the epigallocatechin gallate tetramer is oolong homobisfiavan-tetramer-1 andor oolong homobisflavan-tetramer-2.

4. The method according to claim 1, wherein the epigallocatechin gallate trimer is oolong homobisflavan-trimer-4; and the epigallocatechin gallate tetramer is oolong homobisflavan-tetramer-1.

5. A method for suppressing elevation of blood sugar level, comprising administering to a subject a composition comprising an epigallocatechin gallate dimer, trimer andor tetramer as an active ingredient.

6. A method for inhibiting α-glucosidase, comprising administering to a subject a composition comprising a compound of Formula 1or Formula 2:

[Chem. 1]

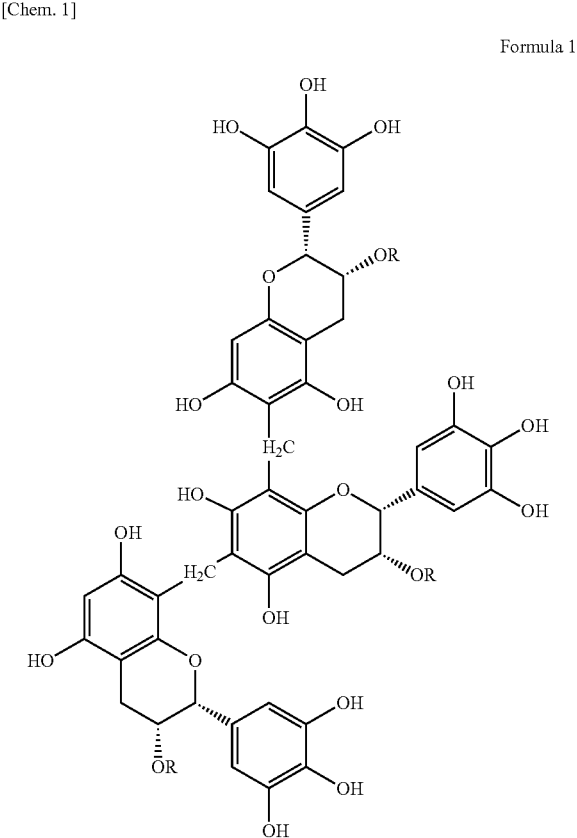

Formula 1

[Chem. 2]

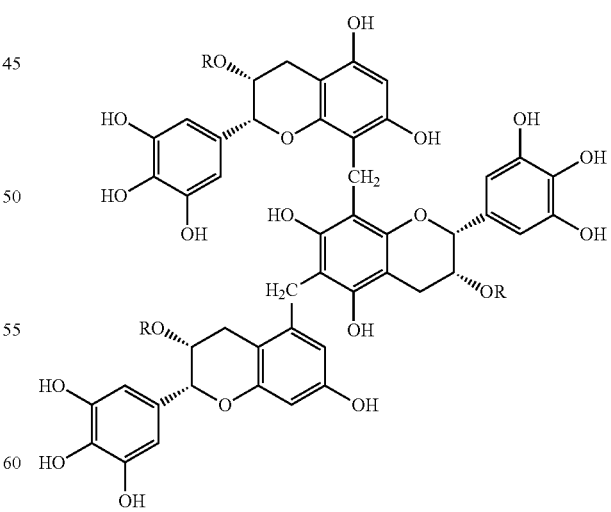

Formula 2 wherein R is galloyl or or a salt thereof.

7. A method for suppressing elevation of blood sugar level, comprising administering to a subject a composition comprising a compound of Formula 1 or Formula 2:

Formula 1

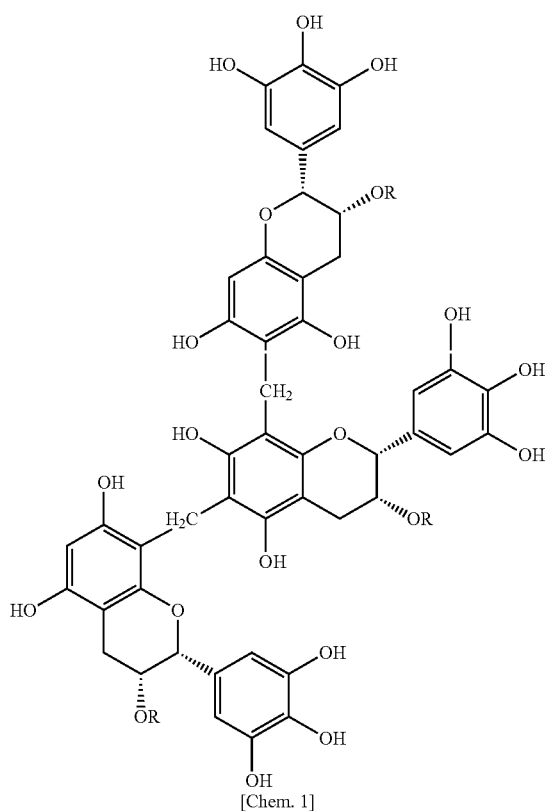

[Chem. 1]

Formula 2

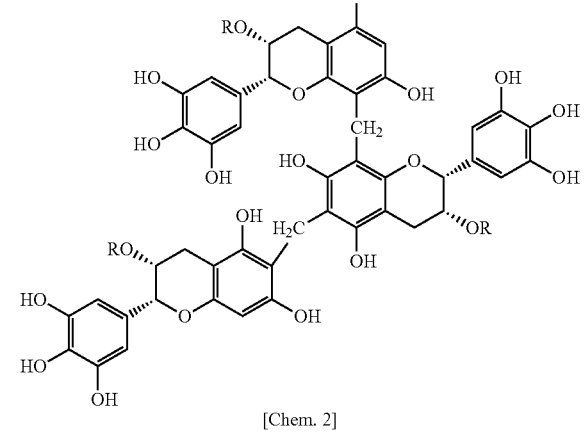

[Chem. 2]

wherein R is galloyl or H, or a salt thereof.

8. The method according to claim 6, wherein R is galloyl.
9. The method according to claim 7, wherein R is galloyl.
10. The method according to claim 1, wherein the active ingredient is the epigallocatechin gallate tetramer.
11. The method according to claim 5, wherein the active ingredient is the epigallocatechin gallate tetramer.

* * * * *